United States Patent
Yan et al.

(10) Patent No.: US 11,026,925 B2
(45) Date of Patent: Jun. 8, 2021

(54) ANGIOTENSIN II RECEPTOR ANTAGONIST METABOLITE AND NEP INHIBITOR COMPOSITE AND PREPARATION METHOD THEREOF

(71) Applicant: SHENZHEN SALUBRIS PHARMACEUTICALS CO. LTD, Shenzhen (CN)

(72) Inventors: Jie Yan, Shenzhen (CN); Wenjie Xu, Shenzhen (CN); Jianqiong Zhi, Shenzhen (CN); Song Li, Shenzhen (CN); Yang Wang, Chengdu (CN); Yanxin Zheng, Shenzhen (CN)

(73) Assignee: SHENZHEN SALUBRIS PHARMACEUTICALS CO. LTD., Shenzhen (CN)

( * ) Notice: Subject to any disclaimer, the term of this patent is extended or adjusted under 35 U.S.C. 154(b) by 355 days.

(21) Appl. No.: 16/071,377

(22) PCT Filed: Jan. 19, 2017

(86) PCT No.: PCT/CN2017/071625
§ 371 (c)(1),
(2) Date: Jul. 19, 2018

(87) PCT Pub. No.: WO2017/125031
PCT Pub. Date: Jul. 27, 2017

(65) Prior Publication Data
US 2020/0061025 A1 Feb. 27, 2020

(30) Foreign Application Priority Data

| Jan. 20, 2016 | (CN) | 201610038846.3 |
| Mar. 30, 2016 | (CN) | 201610193099.0 |
| Jun. 16, 2016 | (CN) | 201610430248.0 |

(51) Int. Cl.
| A61K 31/4178 | (2006.01) |
| A61K 47/55 | (2017.01) |
| A61P 9/04 | (2006.01) |
| A61K 31/197 | (2006.01) |

(52) U.S. Cl.
CPC ........ *A61K 31/4178* (2013.01); *A61K 31/197* (2013.01); *A61K 47/55* (2017.08); *A61P 9/04* (2018.01)

(58) Field of Classification Search
None
See application file for complete search history.

(56) References Cited

U.S. PATENT DOCUMENTS

| 8,877,938 B2 | 11/2014 | Feng et al. |
| 10,537,555 B2* | 1/2020 | Wang .................. A61P 9/04 |
| 2009/0156585 A1 | 6/2009 | Feng et al. |
| 2015/0057322 A1 | 2/2015 | Feng et al. |

FOREIGN PATENT DOCUMENTS

| CN | 101024643 A | 8/2007 |
| CN | 104826115 A | 8/2015 |
| CN | 104826115 A | 8/2015 |
| CN | 105503760 A | 4/2016 |
| CN | 105503760 A | 4/2016 |
| CN | 105669581 A | 6/2016 |
| CN | 105669581 A | 6/2016 |
| CN | 105963296 A | 9/2016 |
| CN | 106138041 A | 11/2016 |
| CN | 106138041 A | 11/2016 |
| CN | 106146472 A | 11/2016 |
| CN | 106146472 A | 11/2016 |
| WO | WO 2007/056546 A1 | 5/2007 |
| WO | WO-2007056546 A1 * | 5/2007 ............. A61K 45/06 |

OTHER PUBLICATIONS

Kavanagh et al. "Pharmaceutical cocrystals: from serendipity to design to application" Drug Discovery Today, 2019, 24, 796. (Year: 2019).*
International Search Report for International Application No. PCT/CN2017/071625 (five pages).
Translation of the International Search Report for International Application No. PCT/CN2017/071625 (four pages).
Tamaki et al., "EXP3174: The Major Active Metabolite of Losartan," *Cardiovascular Drug Reviews*, vol. 15, No. 2, pp. 122-136 (1997).
P.S. Macdonald, "Combined Angiotensin Receptor/Neprilysin Inhibitors: A Review of the New Paradigm in the Management of Chronic Heart Failure," *Clinical Therapeutics*, vol. 37, No. 10, pp. 2199-2205 (2015).
"Assessment Report," Committee for Medicinal Products for Human Use, European Medicines Agency, retrieved from https://www.ema.europa.eu/en/documents/assessment-report/entresto-epar-public-assessment-report_en.pdf (2015) (115 pages).

* cited by examiner

*Primary Examiner* — Amanda L. Aguirre
(74) *Attorney, Agent, or Firm* — Finnegan, Henderson, Farabow, Garret & Dunner, LLP

(57) ABSTRACT

Provided are a supramolecular composite comprising an angiotensin II receptor (AT1) blocking compound, a neutral endopeptidase inhibitor (NEPi), and a pharmaceutically acceptable cation. The invention further provides a method for preparing the composite and an application of the composite for preparing a pharmaceutical product for treating heart failure.

22 Claims, 8 Drawing Sheets

ANGIOTENSIN II RECEPTOR ANTAGONIST METABOLITE AND NEP INHIBITOR COMPOSITE AND PREPARATION METHOD THEREOF

This application is a national stage filing under 35 U.S.C. § 371 of International Application No. PCT/CN2017/071625, filed on Jan. 19, 2017, which claims priority to Chinese Patent Application No. 201610038846.3, filed on Jan. 20, 2016, Chinese Patent Application No. 201610193099.0, filed on Mar. 30, 2016, and Chinese Patent Application No. 201610430248.0, filed on Jun. 16, 2016.

TECHNICAL FIELD

This invention belongs to the pharmaceutical chemistry field, in particularly, involves the compounds of angiotensin II receptor antagonist metabolite and NEP inhibitor, and preparation methods thereof.

BACKGROUND ART

Allisartan isoproxil (CAS: 947331-05-7), chemical name: 2-butyl-4-chloro-1-[2'-(1H-tetrazole-5-yl)-1,1'-biphenyl-methyl]-imidazole-5-carboxylic acid, 1-[(isopropoxy)-carbonyloxy]-methyl ester, trade name: Xinlitan, is a new type of angiotensin II receptor (AT1) antagonist. Its structural formula was first published in Chinese patent CN200610023991.0, and its applications in preparation of antihypertensive medications were also disclosed. Being compared with other same-type anti-hypertensive products (such as losartan), allisartan isoproxil shows low toxicity, good antihypertensive efficacy and other advantages.

Allisartan isoproxil plays a role in the treatment by hydrolyzing and metabolizing to EXP3174. However, EXP3174 shows low bioavailability, and poor therapeutic effect while being singly used as medication, for its strong molecular structure polarity makes it hard to pass through the cell membrane by diffusion or other passive absorption ways like diffusion, and its passive absorptions can only be improved by structure optimization. However, many methods, such as structure optimization, preparation administration optimization reported in prior art can't improve the bioavailability of EXP3174 effectively.

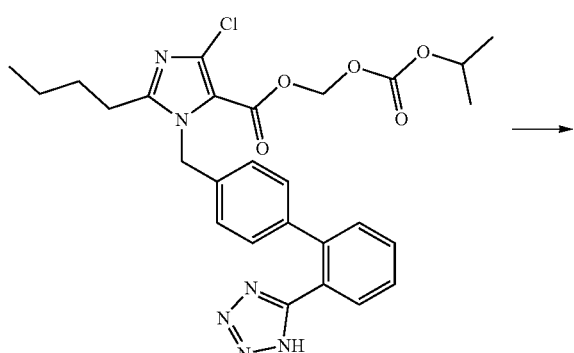

Allisartan Isoproxil

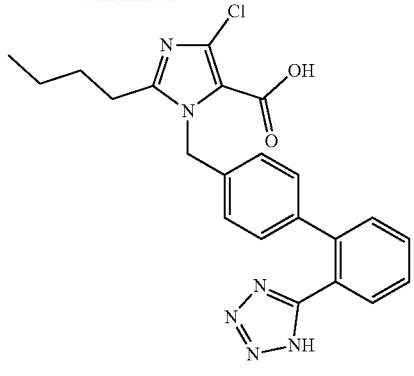

EXP3174

Neprilysin (NEP) is a type of neutral endopeptidase which degrades various endogenous vasoactive peptides, such as natriuretic peptide, bradykinin, and can also reduce the level of adrenomedullin, while neprilysin inhibitor can improve the level of these substances thus to antagonize vasoconstriction, sodium retention and excessive activation of neuroendocrine system.

Hypertension is the most common cardiovascular disease whose clinical syndrome is characterized by the elevation of systemic arterial pressure. It is divided into primary and secondary hypertensions, among which, patients with primary hypertension account for more than 95% of the total patients with hypertension. With the development of social economy, and the improvement of people's living standard, the morbidity of hypertension is continuously increasing. Hypertension, if it can't be controlled and treated effectively, may cause coronary arteriosclerosis thus to develop into coronary heart disease or angina, and may also cause hypertensive heart disease, heart failure and other severe complications. In addition, long-term hypertension may cause kidney, brain, cardiovascular and other organic damages.

As the causes and pathogeneses of hypertension are diverse, inadequate control of blood pressure will affect the structure and function of multiple organs in body, patients with hypertension will also suffer from other organs' diseases or damages, such as cardiovascular and cerebrovascular diseases, hyperlipemia. For the treatment, combination with antihypertensive drugs with different mechanisms is helpful to control the blood pressure more effectively, more importantly, it may show synergistic effect which is helpful to reduce the usage amount of drugs and further reduce the side reactions.

Heart failure (HF for short) is one of the most common cardiovascular diseases at present, which is a group of complex clinical syndromes of ventricular filling or ejection impairment caused by abnormal cardiac structure or function, and mainly clinically manifested as dyspnea and weakness (limited exercise tolerance), as well as fluid retention (pulmonary congestion and peripheral oedema). Heart failure is the serious and end stage of various heart diseases with high morbidity (*China Guideline for Diagnosis and Treatment of Heart Failure*, 2014).

In the past more than a decade, little progress is made for drugs against heart failure. Till now, angiotensin converting enzyme inhibitor (ACEI) is still the first choice which is verified to be capable to reduce the fatality rate of patients, as well as the recognized drug for the treatment of heart failure with the most accumulated evidences-based medicine. For this serial of drugs, the most common side effect is hacking cough with the incidence of 1~30% during the treatment with ACEI, which often occurs in the early stage (from several days to several weeks) of medication, may show cumulative effect; the treatment may also lead to angioneurotic edema. EXP3174 shows potential in the treatment of hypertension, however, being limited by its extremely low bioavailability, which leads to its poorer druggability, further study on its indication is also unable to be carried out.

Since 2005, due to the prevalence of risk factors of cardiovascular disease, the number of patients with cardiovascular disease in our country has been increasing continuously. According to the statistics, patients with cardiovascular diseases in our country are about 290 million, including 270 million patients with hypertension, and about 4,500 thousand patients with heart failure (*Chinese Cardiovascular Disease Report*, 2013).

A sodium salt complex (LCZ696) of Valsartan-Sacubitril and its preparation method were disclosed in patent WO2007056546. Specifically, LCZ696 is supramolecular complex (compound) trisodium salt containing 2.5 molecules crystal water and is composed by bonding of valsartan and AHU377 via non-covalent bonds, the compound shows dual-acting, which is angiotensin receptors blocking and neutral endopeptidase inhibition, clinically shows the effect on lowering blood pressure. The reported clinical experimental data show that, being compared with the enalapril treatment group, LCZ696 reduces the hospitalization rate of patients with heart failure by 21%, and the symptoms of heart failure and physical restraint decreases as well, is superior to enalapril in the reduction of death rate and hospitalization rate for patients with heart failure (N Engl J Med, 2014, 371(1): 993-1004). However, because of the comprehensive influence of components (AT1, NEPi, cation, etc.) forming the compound or other unknown factors, LCZ696 shows easy moisture absorption, and less stability in humidity and thermal conditions, moreover, it is also easy to show electrostatic effect which affects the product's flowability; the properties mentioned above lead to relatively rigorous requirements on the production environment during the preparation of clinical medication of LCZ696. Therefore, to look for a compound that shows good therapeutic effect and little side effect, and used for the treatment of a series of cardiovascular diseases, including hypertension, heart failure, etc. and other complications, and shows the physicochemical property convenient for production is the technical problem which has not been solved according to existing technologies. This invention provides a series of supramolecular complexes (compounds) which are composed of chemical compounds with angiotensin II receptor (AT1) blocking effect and neprilysin inhibitor (NEPi), show dual-acting of both angiotensin II receptor blocking and neutral endopeptidase inhibiting effects, and have more beneficial physicochemical properties during production.

CONTENTS OF THE INVENTION

The first objective of this invention is to overcome the shortcomings of existing technologies, and provides a series of supramolecular complexes (compounds) with dual-acting; the supramolecular complexes (compounds) are composed as follows:
1) Chemical compound with angiotensin II receptor (AT1) blocking effect;
2) Neprilysin inhibitor (NEPi);
3) Pharmaceutically acceptable cation.

In one embodiment, the compound with angiotensin II receptor (AT1) blocking effect is allisartan isoproxil metabolite (EXP3174), its chemical formula is $C_{22}H_{21}ClN_6O_2$, and the structure is shown as below:

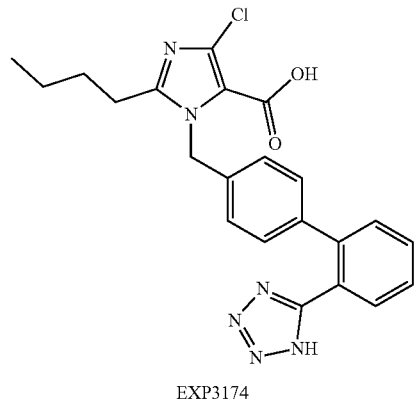 [SMILES: CCCCc1nc(Cl)c(C(=O)O)n1Cc1ccc(-c2ccccc2-c2nnn[nH]2)cc1]

EXP3174

In one embodiment, the neprilysin inhibitor (NEPi) is AHU377 (Sacubitril, CAS: 149709-62-6), its chemical formula is $C_{24}H_{29}NO_5$, and the structure is shown as below:

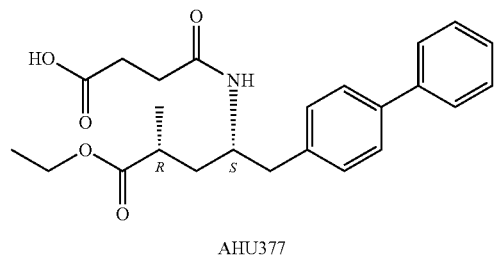

AHU377

The AHU377 mentioned above is a type of specific neprilysin inhibitors and is first disclosed in the U.S. Pat. No. 5,217,996.

In one embodiment, the pharmaceutically acceptable cation mentioned is calcium ion ($Ca^{2+}$). The known technologies consider that the angiotensin II receptor (AT1) blocking compounds can combine with any cation to form supramolecular complex, however, the inventor found after experiments that, supramolecular complexes are formed with other cations, such as sodion ($Na^+$), potassium ion ($K^+$), can't be obtained as expected.

The supramolecular complex (compound) is composed of the bonding of above-mentioned compound with angiotensin II receptor (AT1) blocking effect, neprilysin inhibitor and pharmaceutically acceptable cation by non-covalent bonds, among which, the mentioned non-covalent bonds are known to person skilled in the art, which include but are not limited to hydrogen bond, coordination bond, ionic bond, allisartan isoproxil metabolite (EXP3174) contains two acidic groups, namely, carboxylic acid and tetrazole, and AHU377 contains one type of acidic group, namely, carboxylic acid.

The mentioned supramolecular complex (compound) can further contain solvents. The mentioned solvents are packed and/or held back in the crystal lattices as a part of molecule, which contribute to the intramolecular structure, such as supramolecular interaction. The mentioned solvents are the common solvents in the art, such as water, methanol, ethanol, 2-propyl alcohol, acetone, ethyl acetate, methyl-tert-butyl ether, acetonitrile, methylbenzene, dichloromethane, in which, water is preferred. The mentioned supramolecular complex (compound) can also be deemed as calcium salt solvate.

In one embodiment, the formula unit of mentioned supramolecular complex (compound) is shown as below:

(aEXP3174.bAHU377).xCa.nA

Wherein, the molar ratio of allisartan isoproxil metabolite (EXP3174) to AHU377 (a to b) is 1:0.25~4, in embodiments, the values of a to b can be 1:0.25, 1:0.5, 1:1, 1:1.5, 1:2, 1:2.5, 1:3, 1:3.5, 1:4, etc.; relative to the molar ratio of allisartan isoproxil metabolite (EXP3174), the molar ratio x of $Ca^{2+}$ can be 0.5~3, such as 0.5, 1, 1.5, 2, 2.5, 3; A in the mentioned supramolecular complex (compound) refers to water, methanol, ethanol, 2-propyl alcohol, acetone, ethyl acetate, methyl-tert-butyl ether, acetonitrile, methylbenzene, dichloromethane or other solvents, and relative to the molar ratio of allisartan isoproxil metabolite (EXP3174), the molar ratio n of solvent is 0~3, such as 0, 0.5, 1, 1.5, 2, 2.5, 3.

Moreover, in one embodiment of the mentioned supramolecular complex (compound), the molar ratio of allisartan isoproxil metabolite (EXP3174) to AHU377 (a to b) is 1:1, and the solvent is water; allisartan isoproxil metabolite (EXP3174) contains two types of acidic groups, namely, carboxylic acid and tetrazole, AHU377 contains one type of acidic group, namely, carboxylic acid, allisartan isoproxil metabolite (EXP3174) and AHU377 which bond with calcium ion by ionic bond and/or coordination bond and other non-covalent bonds, can also be deemed as a calcium salt solvate.

In one embodiment, the formula unit of mentioned supramolecule is as below:

(EXP3174.AHU377).xCa.n$H_2O$

Wherein, the molar ratio x of $Ca^{2+}$ is 0.5~2, such as 0.5, 1, 1.5, 2; the molar ratio n of solvent is 0~3, such as 0, 0.5, 1, 1.5, 2, 2.5, 3.

In one embodiment, the mentioned supramolecular complex (compound) is composed of 1 molar ratio of allisartan isoproxil metabolite (EXP3174), 1 molar ratio of AHU377 and 1.5~2 molar ratios of $Ca^{2+}$ via non-covalent bond, and contains 1~3 molar ratios of water molecules, in which, the molar ratio value of $Ca^{2+}$ can be 1.5 or 2, that of water can be 1, 1.5, 2, 2.5 or 3, and 2~3 molar ratios of water molecules are preferred, wherein, the molar ratio of $Ca^{2+}$ can be 1.5 or 2, while that of water can be 2, 2.5 or 3, and in preferred embodiments, the formula unit of the mentioned supramolecular complex (compound) is shown as below:

(EXP3174.AHU377).1.5Ca.n$H_2O$ (n is an arbitrary value from 1 to 3, and an arbitrary value from 2 to 3 is preferred)

For example, it can be (EXP3174.AHU377).1.5Ca.1$H_2O$;
(EXP3174.AHU377).1.5Ca.1.5$H_2O$;
(EXP3174.AHU377).1.5Ca.2$H_2O$;
(EXP3174.AHU377).1.5Ca.2.5$H_2O$;
(EXP3174.AHU377).1.5Ca.3$H_2O$;

Or, the formula unit of the mentioned supramolecular complex (compound) is shown as below:

(EXP3174.AHU377).2Ca.n$H_2O$ (n is an arbitrary value from 1 to 3, and an arbitrary value from 2 to 3 is preferred)

For example, it can be (EXP3174.AHU377).2Ca.1$H_2O$;
(EXP3174.AHU377).2Ca.1.5$H_2O$;
(EXP3174.AHU377).2Ca.2$H_2O$;
(EXP3174.AHU377).2Ca.2.5$H_2O$;
(EXP3174.AHU377).2Ca.3$H_2O$;

It is understood by the person skilled in the art that the allisartan isoproxil metabolite (EXP3174), AHU377, $Ca^{2+}$ and solvent molecules will fill in the structure cells of supramolecular complex (compound) in the form of several formula units.

The supramolecular complex (compound) differs from the physical mixture obtained by simple mixing of two active ingredients. The supramolecular complex (compound) obtained significantly differs from EXP3174 and AHU377 calcium salts in XRD spectrum, and solubility property in various solvents (such as water, ethanol, ethanol-water), as well as other physical properties or chemical properties, such as hygroscopicity, melting point, and infrared spectrum.

For one obtained supramolecular complex (compound) in this invention, its X-ray powder diffraction (XRD) spectrum shows diffraction peaks with comparatively strong absorption intensity at 4.35°, 5.15°, 5.90°, 12.80° and 15.85° with the acceptable error range of ±0.2°, for the peaks with strong absorption intensity, they are seldom affected by product feature, test instrument, test conditions and other factors, therefore, the reproducibility is very high, it can also be understood by the person skilled in the art that, for specific compounds, which is affected by product feature, test instrument, test conditions and other factors, the reproducibility of the peaks with relatively weak absorption intensity may be not high, and the inventor also found the phenomenon in the repeated tests, the supramolecular complex (compound) samples from same batch/different batches also shows the reproducibility features mentioned above. Furthermore, the X-ray powder diffraction (XRD) spectrum of the supramolecular complex (compound) shows diffraction peaks with stronger repeatability in 9.00°, 10.15° and 15.02° with the acceptable error range of ±0.2°; more specifically, the X-ray powder diffraction spectrum of supramolecular complex (compound) shows the following peaks in one test:

| Number | 2θ (°, ±0.2) | Relative intensity (%) |
|---|---|---|
| 1 | 4.35 | 70.97 |
| 2 | 5.15 | 100.00 |
| 3 | 5.90 | 32.67 |
| 4 | 9.00 | 2.80 |
| 5 | 10.15 | 3.40 |
| 6 | 12.80 | 5.21 |
| 7 | 15.02 | 5.59 |
| 8 | 15.85 | 8.27 |
| 9 | 16.81 | 2.57 |
| 10 | 20.27 | 2.39 |
| 11 | 22.09 | 2.48 |
| 12 | 23.79 | 1.34 |
| 13 | 26.22 | 1.87 |

The XRD spectrum of the supramolecular complex (compound) is shown in FIG. 1. The molar ratio of EXP3174 to AHU377 in the supramolecular complex (compound) can be directly/indirectly obtained via the content analytical method, for example, the mass/content of EXP3174 and AHU377 (free acid) in supramolecular complex (compound) can be determined by high-performance liquid chromatography (HPLC), and the molar ratio of 1:1 can be obtained by further conversion.

The differential scanning calorimetry (DSC) of the supramolecular complex (compound) shows two dehydration endothermic peaks at 94.4±10° C. and 164.1±10° C., as the supramolecular complex (compound) contains crystal waters, the person skilled in the art can understand that, under different test conditions, such as heating rate, and different sample characteristics, such as sample grain size, some peaks (such as dehydration endothermic peak) in DSC spectrum may show big fluctuation, for example, the dehydration endothermic peak's positions in spectrums obtained under different heating rates have a relatively big differences, and there is another endothermic peak in the spectrum at 244.6±5° C. More specifically, the DSC of this example's supramolecular complex (compound) is shown in FIG. 2.

The Raman spectrum of the supramolecular complex (compound) shows diffraction peaks at the wavelength of ($cm^{-1}$) 3,061 (m), 2,935 (m, wide), 1,613 (st), 1,521 (m), 1,482 (w), 1,286 (m), 995 (w), 816 (w, wide), and 408 (w), and the intensities at the absorption wavebands are expressed as below, (w)=weak, (m)=medium and (st)=strong.

The infrared spectrum ($cm^{-1}$) of the supramolecular complex (compound) shows diffraction peaks at the important wavebands of 3,383 (st, wide), 1,709 (m), 1,634 (m), 1,577 (st), 1,549 (st), 1,459 (st), 1,407 (st), 1,262 (m), 1,173 (w), 762 (m), 698 (w), etc. The intensities at the absorption wavebands are expressed as below, (w)=weak, (m)=medium and (st)=strong.

For the test of water content in the supramolecular complex (compound), the methods commonly used in the art, such as Karl Fischer method and/or thermogravimetry can be adopted. Specifically, the thermogravimetric analysis spectrum (TG) of the supramolecular complex (compound) shows that the water content of the supramolecular complex (compound) is 5.0%, while the water content is determined to be 4.9% by Karl Fischer method.

The atomic absorption spectrum of the supramolecular complex (compound) shows that the calcium content of the supramolecular complex (compound) is 6.46%.

The measured values of elemental analysis of the supramolecular complex (compound) are C: 57.81%, H: 5.48%, and N: 10.36%.

Judged from the information above, the formula unit of the supramolecular complex (compound) is $(EXP3174 \cdot AHU377)^{3-} \cdot 1.5Ca^{2+} \cdot 2.5H_2O$.

For the other obtained supramolecular complex (compound) mentioned in this invention, its XRD spectrum is similar to that of above-mentioned supramolecular complex (compound). Specifically, its XRD spectrum shows diffraction peaks with relatively strong absorption intensity at 4.40°, 5.19° and 5.96° with the acceptable error range of ±0.2°; furthermore, its XRD spectrum also shows diffraction peaks with comparatively strong repeatability at 15.82° and 26.34° with the acceptable error range of ±0.2°; more specifically, the XRD spectrum of the supramolecular complex (compound) h the following peaks in a test:

| Number | 2θ (°, ±0.2) | Relative intensity (%) |
|---|---|---|
| 1 | 4.40 | 77.30 |
| 2 | 5.19 | 100.00 |
| 3 | 5.96 | 19.78 |
| 4 | 15.82 | 5.11 |
| 5 | 26.34 | 3.44 |

The XRD spectrum of the supramolecular complex (compound) is shown in FIG. 5. The molar ratio of EXP3174 to AHU377 in supramolecular complex (compound) can be directly/indirectly obtained with the content analytical method, for example, the mass/content of EXP3174 and AHU377 (free acid) in supramolecular complex (compound) can be determined by HPLC, and the molar ratio of 1:1 can be obtained by further conversion.

The DSC of the supramolecular complex (compound) shows that there are two dehydration endothermic peaks at 95.4±10° C. and 166.4±10° C., as the supramolecular complex (compound) contains crystal waters, the person skilled in the art can understand that, under different test conditions, such as heating rate, and different sample characteristics, such as sample grain size, partial peaks (such as dehydration endothermic peak) in DSC spectrum may show big fluctuation, for example, the dehydration endothermic peak's positions in spectrums obtained under different heating rates have a relatively big differences, and there is another endothermic peak in the spectrum at 242.4±5° C. More specifically, it finds that, after multiple repeats, the difference of the DSC objectively exists between the supramolecular complex (compound) prepared by different examples, and the DSC of this example's supramolecular complex (compound) is shown in FIG. 6.

For the test of water content in the supramolecular complex (compound), the methods commonly used in the art, such as Karl Fischer method and/or thermogravimetry can be adopted. Specifically, it finds that, after multiple repeats, the difference of TG between the supramolecular complex (compound) and the previous supramolecular complex objectively exist, more specifically, the spectrum shows that the water content of the supramolecular complex (compound) is 3.97%, while the water content is determined to be 3.83% by Karl Fischer method.

The atomic absorption spectrum of the supramolecular complex (compound) shows that the calcium content of the supramolecular complex (compound) is 6.50%.

The measured values of elemental analysis of the supramolecular complex (compound) are C: 58.51%, H: 5.41%, and N: 10.25%.

Judged from the information above, the formula unit of the supramolecular complex (compound) is $(EXP3174 \cdot AHU377)^{3-} \cdot 1.5Ca^{2+} \cdot 2H_2O$.

Another objective of this invention is to provide a preparation method for a series of supramolecular complexes (compounds) mentioned in this invention, and the following steps are included:

1) The compound with angiotensin II receptor (AT1) blocking effect and neprilysin inhibitor (NEPi) are dissolved in suitable solvent;
2) The pharmaceutically acceptable calcium ionic salt and/or calcium ion hydroxide are/is dissolved or suspended in suitable solvent;
3) The mixture obtained in step 2) is slowly added to the solution obtained in step 1), or calcium ionic salt and/or calcium ion hydroxide (directly in solid form) are/is respectively added with solvent to the reaction system in order, and the mixture is stirred for complete crystallization;
4) The solid is precipitated and dried to obtain the mentioned supramolecular complex (compound).

The reaction can be performed under the reaction temperatures known by the person skilled in the art, such as the reaction temperatures includes low temperature, room temperature or warming, in which, the temperature is between room temperature and 45° C. preferably, and the room temperature mentioned means 20±10° C.

Specifically, the preparation of the mentioned series of supramolecular complexes (compounds) can be affected by the rate of added amount, reaction solvents and other factors, so it's not easy to obtain a stable preparation method, in which, the compound with angiotensin II receptor (AT1)

blocking effect and neprilysin inhibitor (NEPi) are free substances which can be obtained via directly using free substance or via freeing corresponding salt; the selection of reaction solvents has influence on obtaining the mentioned series of supramolecular complexes (compounds), manifested as that the supramolecular complex (compound) can't be obtained as expected via some tested solvent systems, specifically, the mentioned solvent system which can get the compound contains acetone and/or isopropanol, and the added amounts of mentioned angiotensin II receptor (AT1) blocking effect and neprilysin inhibitor (NEPi) are basically the same as the molar ratio of the two molecules in the structure of supramolecular complex (compound);

The calcium ionic salts mentioned in step 2) are common calcium ionic salts in the art, such as $CaCl_2$, $CaSO_4$, calcium ion hydroxide means $Ca(OH)_2$ which is preferred; the quantity of $Ca^{2+}$ in mentioned calcium ion salts basically corresponds to the ratio of $Ca^{2+}$ in the structure of supramolecular complex (compound).

Specifically, for the specific preparation method of supramolecular complex (compound), the following preparation steps are included:
1) The AHU377 salt is freed to obtain the solution containing AHU377 free acid, and the solvent is removed;
2) The AHU377 free acid obtained in step 1) and EXP3174 are dissolved in organic solvent;
3) The pharmaceutically acceptable calcium ionic salt and/or calcium ion hydroxide are/is dissolved or suspended in suitable solvent;
4) The mixture obtained in step 3) is added to the solution obtained in step 2) slowly, or calcium ionic salt and/or calcium ion hydroxide (directly in solid form) are/is respectively added with solvent to the reaction system in order;
5) The resulting mixture is stirred for complete crystallization, filtered to obtain the solid precipitations, and dried to obtain the mentioned supramolecular complex (compound).

The salts of AHU377 mentioned in step 1) are common metal/non-metal salts, such as a calcium salt, a magnesium salt, a zinc salt, a ferric salt, a sodium salt, an ammonium salt, a diethylammonium salt, or a triethylammonium salt, in which, $Ca(OH)_2$ is preferred; for the solvent mentioned, isopropyl acetate is preferred;

Specifically, while preparing the supramolecular complex (compound) containing 1.5 molecules calcium ion, that is (EXP3174.AHU377).1.5Ca.nH$_2$O, 0.7~1.2:1 is preferred as the molar ratio of EXP3174 to AHU377 mentioned in step 2);

For the calcium ionic salt and/or calcium ion hydroxide mentioned in step 3), calcium ion hydroxide, that is $Ca(OH)_2$ is preferred, specifically, when preparing the supramolecular complex (compound) containing 1.5 molecules calcium positive ion, the molar ratio of quantity of calcium ion in mentioned calcium ionic salt to AHU377 is 1.3~2:1; for the suitable solvent mentioned, acetone and/or isopropanol are preferred; in addition, a suitable quantity of water needs to be added to the system, 1~8:1 g/ml is preferred as the weight/volume ratio of AHU377 to water, addition with different quantities of water can obtain the supramolecular complexes (compounds) containing different crystal waters; specifically, addition with less quantity of water within the range of suitable quantity is favorable to obtain the supramolecular complex (compound) with fewer crystal waters, while addition with more quantity of water within the range of suitable quantity is favorable to obtain the supramolecular complex (compound) with more crystal waters; more specifically, as described in Example 2, when the weight/volume ratio of AHU377 to water is 2.36:1 g/ml, the formula unit of supramolecular complex (compound) obtained from the reaction is (EXP3174.AHU377).1.5Ca.2.5H$_2$O, and as described in Example 3, when the weight/volume ratio of AHU377 to water is 3.93:1 g/ml, the formula unit of supramolecular complex (compound) obtained from the reaction is (EXP3174.AHU377).1.5Ca.2H$_2$O;

The temperature mentioned in step 4) can be the reaction temperature well known by the person skilled in the art, in which, the temperature between room temperature and 45° C. is preferred, and the room temperature mentioned means 20±10° C.

The supramolecular complex (compound) mentioned in the first objective of this invention can be obtained by using the above-mentioned method, and the formula unit of supramolecular complex (compound) obtained preferably using the specific ways of above-mentioned method is selected from any of the following formula units:
(EXP3174.AHU377).1.5Ca.1H$_2$O;
(EXP3174.AHU377).1.5Ca.1.5H$_2$O;
(EXP3174.AHU377).1.5Ca.2H$_2$O;
(EXP3174.AHU377).1.5Ca.2.5H$_2$O;
(EXP3174.AHU377).1.5Ca.3H$_2$O;
(EXP3174.AHU377).2Ca.1H$_2$O;
(EXP3174.AHU377).2Ca.1.5H$_2$O;
(EXP3174.AHU377).2Ca.2H$_2$O;
(EXP3174.AHU377).2Ca.2.5H$_2$O;
(EXP3174.AHU377).2Ca.3H$_2$O.

The third objective of this invention is to provide a kind of supramolecular complex (compound) of this invention in the preparation of a drug for the treatment of a series of cardiovascular diseases, including hypertension, heart failure and other complications.

Specifically, the diseases/complications mentioned include but are not limited to hypertension, acute and chronic heart failure, congestive heart failure, arrhythmia, atrial fibrillation, myocardial infarction, arteriosclerosis, coronary heart disease, instable or stable angina pectoris, pulmonary hypertension, renovascular hypertension, etc., as well as other damages of kidney, brain, heart and other organs caused by long-term hypertension.

The drug mentioned is composed of the supramolecular complex (compound) of the invention and pharmaceutical carrier, in which, the mass percentage of supramolecular complex (compound) mentioned in this invention is 0.1~99.9% in the drug.

Being compared to the single ingredient, analogues disclosed in existing technologies, the mixture obtained by physical mixing, as well as similar products, the supramolecular complexes (compounds) of this invention show advantages in solubility, stability, etc., further corresponding to better clinical therapeutic effect and druggability, and more applicable while applying in production and treatment.

The drug carriers mentioned include but are not limited to the mixture obtained by mixing one or more in filler, disintegrant, binder, lubricant, surfactant, etc. in arbitrary proportion.

The drug mentioned includes but is not limited to capsules, powders, granules, tablets, injections, etc.

The person skilled in the art can prove the supramolecular complexes (compounds) of this invention have advantages in solubility, hygroscopicity, stability and other aspects by solubility and other relevant experiments, or select relevant experimental model to prove the efficacy of the supramolecular complexes (compounds) mentioned in this invention while using in drugs for the treatment of the mentioned series of cardiovascular diseases, such as hypertension and heart failure and other complications.

Specifically, as the supramolecular complexes (compounds) respectively obtained in Examples 2 and 3 of this invention, whose solubility property is significantly improved compared with EXP3174, for example, it shows better solubility in water, ethanol, ethanol-water and other common solvents; in addition, the supramolecular complex (compound) obtained in this invention shows advantages in hygroscopicity compared with the mixture obtained by physical mixing in the same proportion and analogues disclosed in existing technologies.

Animal model is used to comprehensively evaluate the short-term, acute as well as long-term, chronic activity of compounds obtained.

Specifically, the anti-heart failure activities (short-term, acute) of supramolecular complexes (compounds) obtained in Example 2 and Example 3 are tested in animal model (rat), the ligation of left anterior descending coronary artery is used to prepare the animal model with heart failure, the therapeutic drug is administered to the modeling animal via pre-gavage, once per day for 7 continuous days, the rat is continuously administrated for three days after successful modeling. The experiment finds that the compounds obtained show advantage on lowering blood pressure which is significantly superior to that of single administration, and the result is in accordance with what is expected.

The anti-heart failure activity (long-term, chronic) of supramolecular complexes (compounds) obtained in Example 2 and Example 3 is further tested in animal model (rat), the ligation of left anterior descending coronary artery is adopted to prepare the animal model with heart failure, the therapeutic drug is administrated to the animal after a week of postoperative recovery by gavage, once per day for 4 continuous weeks, the experiment finds that the compounds obtained show advantage on treating heart failure which is significantly superior to that of single administration, and which is significantly superior to that of physical mixture.

The person skilled in the art can understand that the therapeutic effect of short-term administration (short-term, acute animal model with heart failure) on test animals can be observed as the effect on lowering blood pressure, while the long-term administration (long-term, chronic animal model with heart failure) is observed as the effect on treating heart failure.

Comprehensive experimental results show that, being compared with the indexes of untreated rats in heart failure model group, those of rats in the compound group are significantly improved; all indexes of animals in compound group also close to that of healthy animals in the blank group; being compared with single drug group with the same dose, the compound group can significantly and preferably delay the process of heart failure of rats, and show significantly better anti-heart failure activity being compared with single administration.

The experimental results also indicate that the series of supramolecular complexes (compounds) in this invention also show advantages of physicochemical property compared with the similar supramolecular complex (compound) that had been disclosed; specifically, the hygroscopicity of the series of supramolecular complexes (compounds) in this invention are better than that of LCZ696, which showed that LCZ696 is more easily hygroscopic than supramolecular complexes (compounds) in this invention under the same condition; in addition, the flowability of the series of supramolecular complexes (compounds) in this invention are also better than that of LCZ696, which shows that, under the same powder property test condition, LCZ696 is hardly flowable, while the flowability of the series of supramolecular complexes (compounds) in this invention is relatively more beneficial for production process, and the electrostatic effect of the supramolecular complexes (compounds) in this invention are significantly improved than that of LCZ696.

The following advantages and beneficial effects are included in this invention relatively to existing technology:

1. A series of supramolecular complexes (compounds) with dual-acting and composed of allisartan isoproxil metabolite (EXP3174) and neprilysin inhibitor (AHU377) are provided in this invention, and they show advantages of therapeutic effect, hygroscopicity, flowability and other aspects compared with the products disclosed in prior art;
2. Preparation methods of supramolecular complexes (compounds) mentioned in this invention are provided;
3. The use of supramolecular complexes (compounds) in this invention for the preparation of drugs treating a series of cardiovascular diseases, such as hypertension, heart failure, and other complications, are provided.

DETAILED DESCRIPTION OF THE EXAMPLES

The invention was further described in detail in combination with Examples and Figures below, but was not limited to these.

In the following Examples:

X-ray powder diffraction was tested by Empyrean X-ray diffractometer with the test condition of Cu target K$\alpha$-ray, voltage: 40 KV, current: 40 mA, emission slit: 1/32°, anti-scattering slit: 1/16°, anti-scattering slit: 7.5 mm, 2$\theta$ range: 3°-60°, step length: 0.02°, and duration of each step: 40 s.

DSC was tested by DSC204F1 differential scanning calorimeter manufactured by NETZSCH, Germany, with the test condition of atmosphere: $N_2$, 20 mL/min; scanner: heat from room temperature to 250° C. at the rate of 10° C./min, and recorded the heating curve.

Water content was tested by TG209 thermal gravimetric analyzer manufactured by NETZSCH, Germany with the test condition of atmosphere: $N_2$, 20 mL/min; scanner: room temperature to 700° C., heating rate: 10° C./min.

EXP3174 used in Example was self-made by the company with the purity of 98.3%. AHU377 calcium salt used in Example was self-made by the company with the purity of 99.4%.

Example 1

Preparation of AHU377 Free Acid:

2.1 g of AHU377 calcium salt and 40 mL of isopropyl acetate were added to a 250 mL single-mouth flask, then 4.5 mL of 2 mol/L hydrochloric acid was added at room temperature, and was stirred to dissolve. The liquid was separated, the organic layer was collected, and washed with 20 mL of water twice; solvent was removed under vacuum at 35° C. to obtain AHU377 free acid.

Example 2

Preparation of Compound:

Under room temperature, 2.36 g of AHU377 free acid prepared in accordance with the method in Example 1, 2 g of EXP3174 and 40 mL of acetone were added to a 250 mL three-mouth flask, and mixture was dissolved to clarification; under room temperature, 1.3 equivalent calcium hydroxide solid corresponding to AHU377 and 1 mL of water were added, being stirred for 10 h at room temperature, 40 mL of acetone was supplemented, and then was reacted for 8 h, through a Buchner funnel was filtered under the protection of nitrogen, the solid was washed with acetone to obtain white solid, 3.5 g solid with the purity of 99%/o by test of HPLC was obtained after being dried under vacuum at 35° C., and in the product the molar ratio of EXP3174 to AHU377 was 1:1 via calculation.

Figure 1:
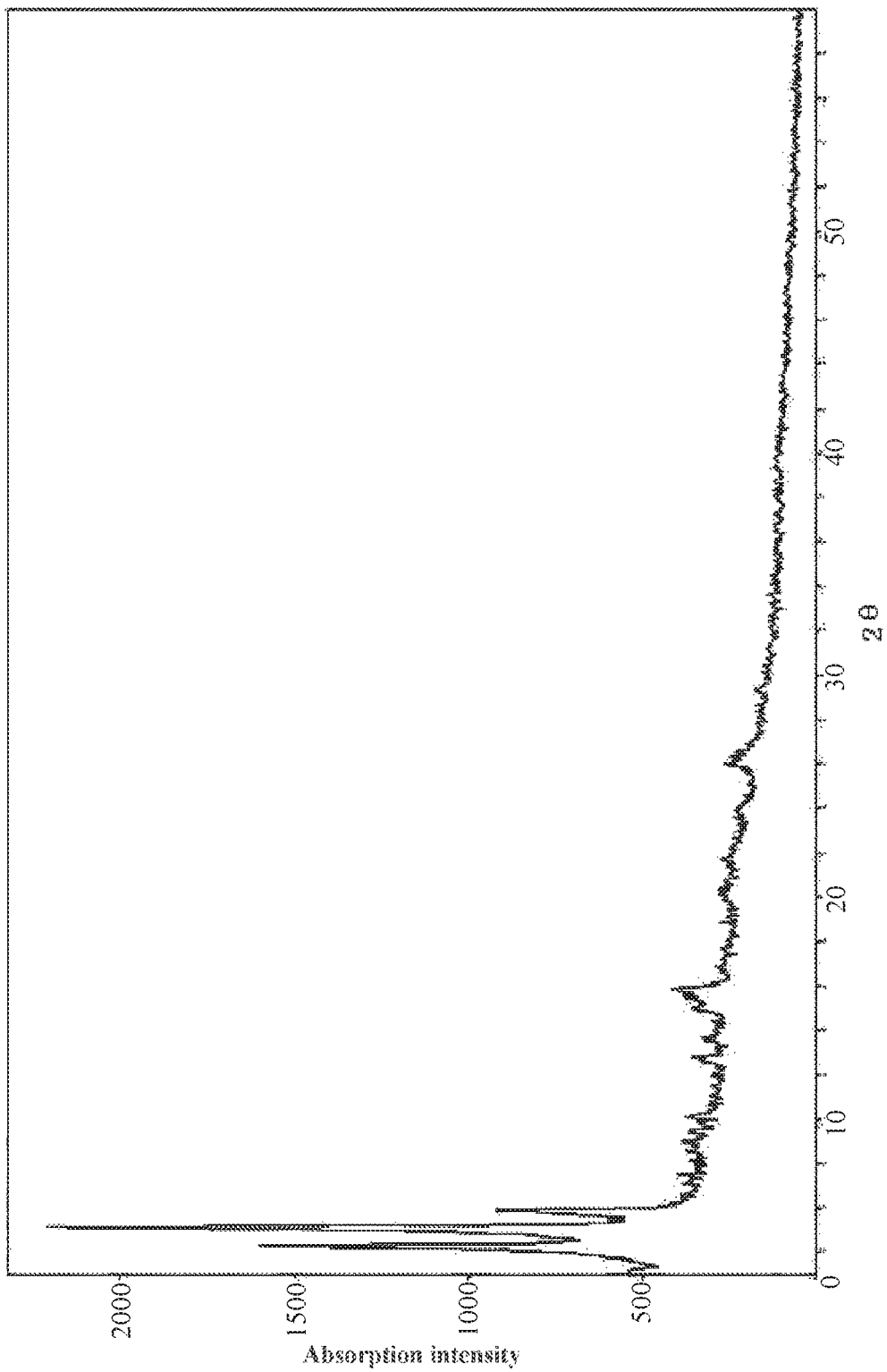
FIG. 1 XRD spectrum of compound obtained in Example 2
Figure 2:
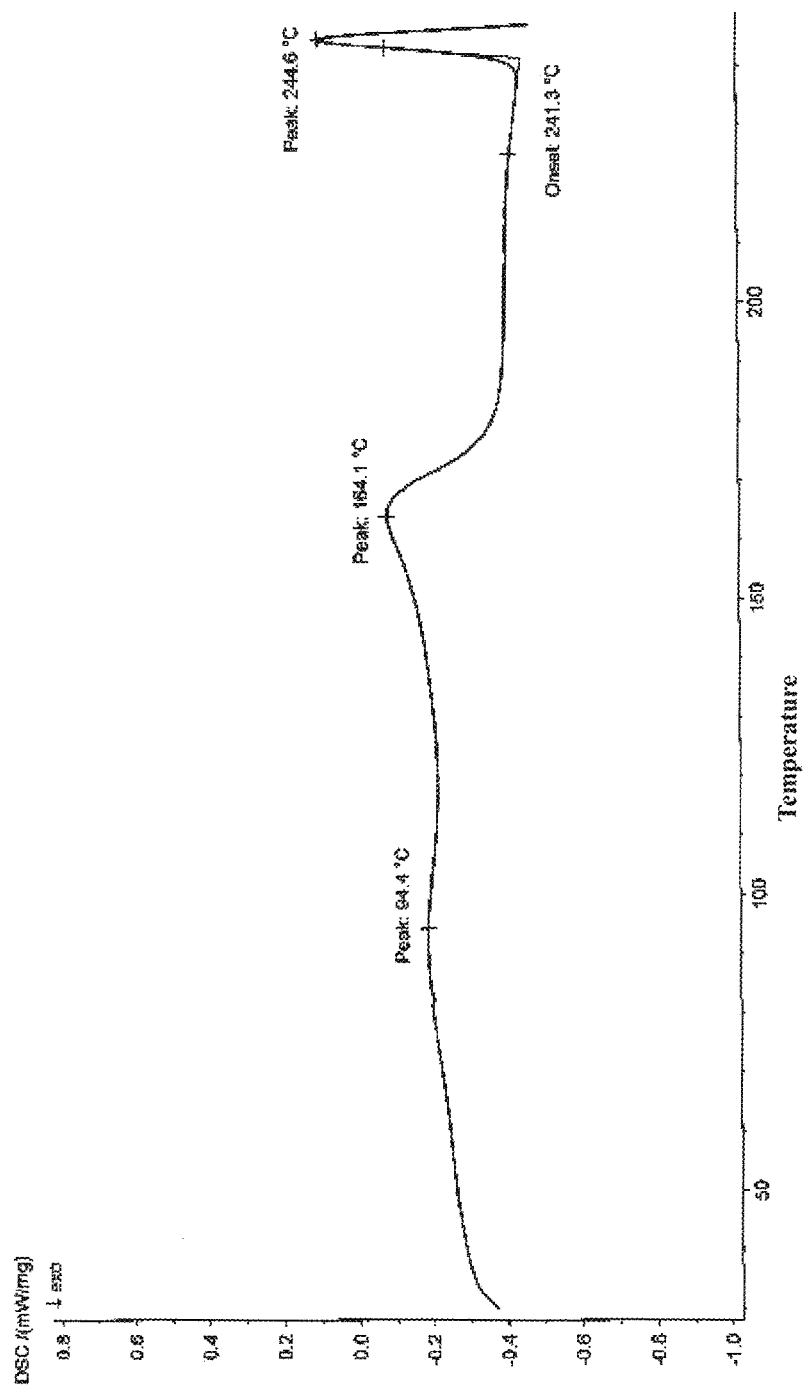
FIG. 2 DSC spectrum of compound obtained in Example 2

The XRD of product obtained was shown as FIG. 1, and DSC spectrum was shown as FIG. 2.

Figure 3:
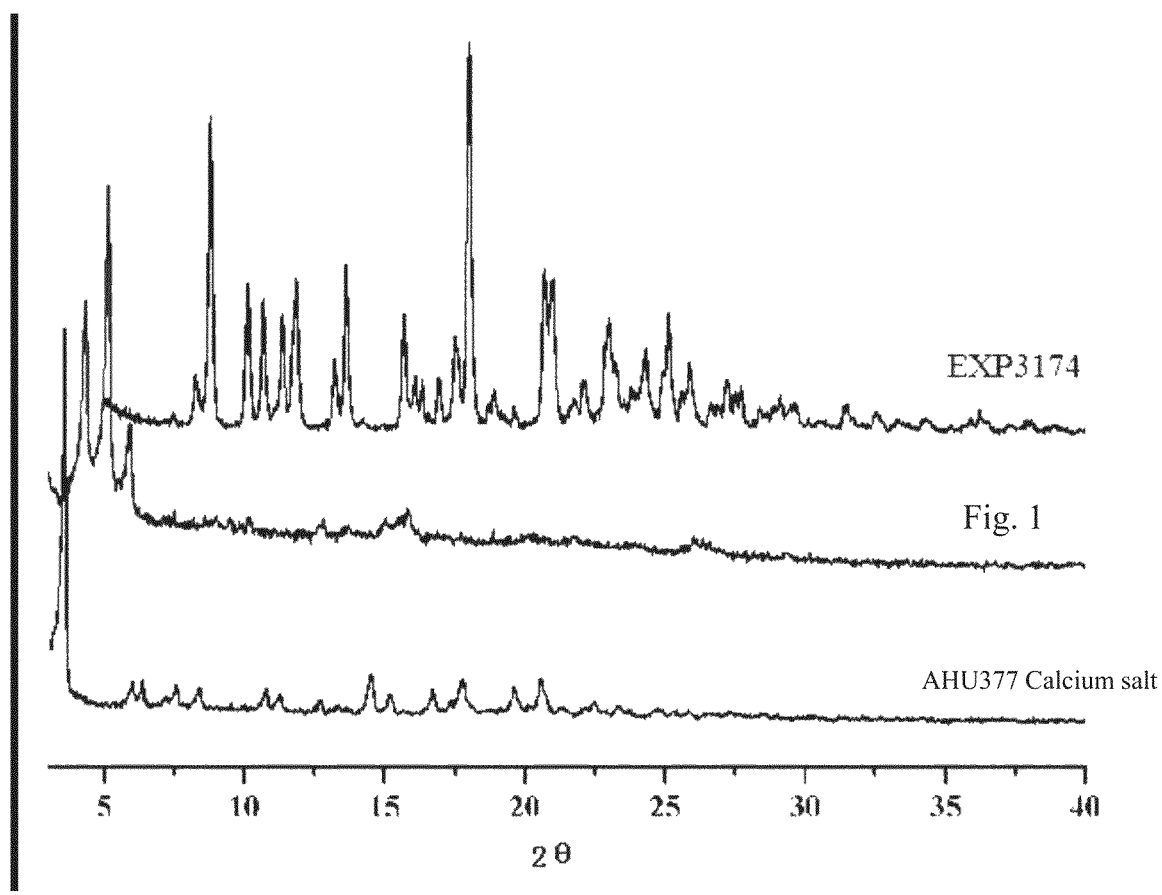
FIG. 3 XRD spectrum comparison of EXP3174, AHU377 calcium salt and compound obtained in Example 2

Being compared with the XRD spectra of EXP3174 and AHU377 calcium salt, it was found that (as shown in FIG. 3), the product obtained was significantly different, and it was determined that the obtained product was obtained as compound by comprehensive analysis of XRD spectrum and HPLC test.

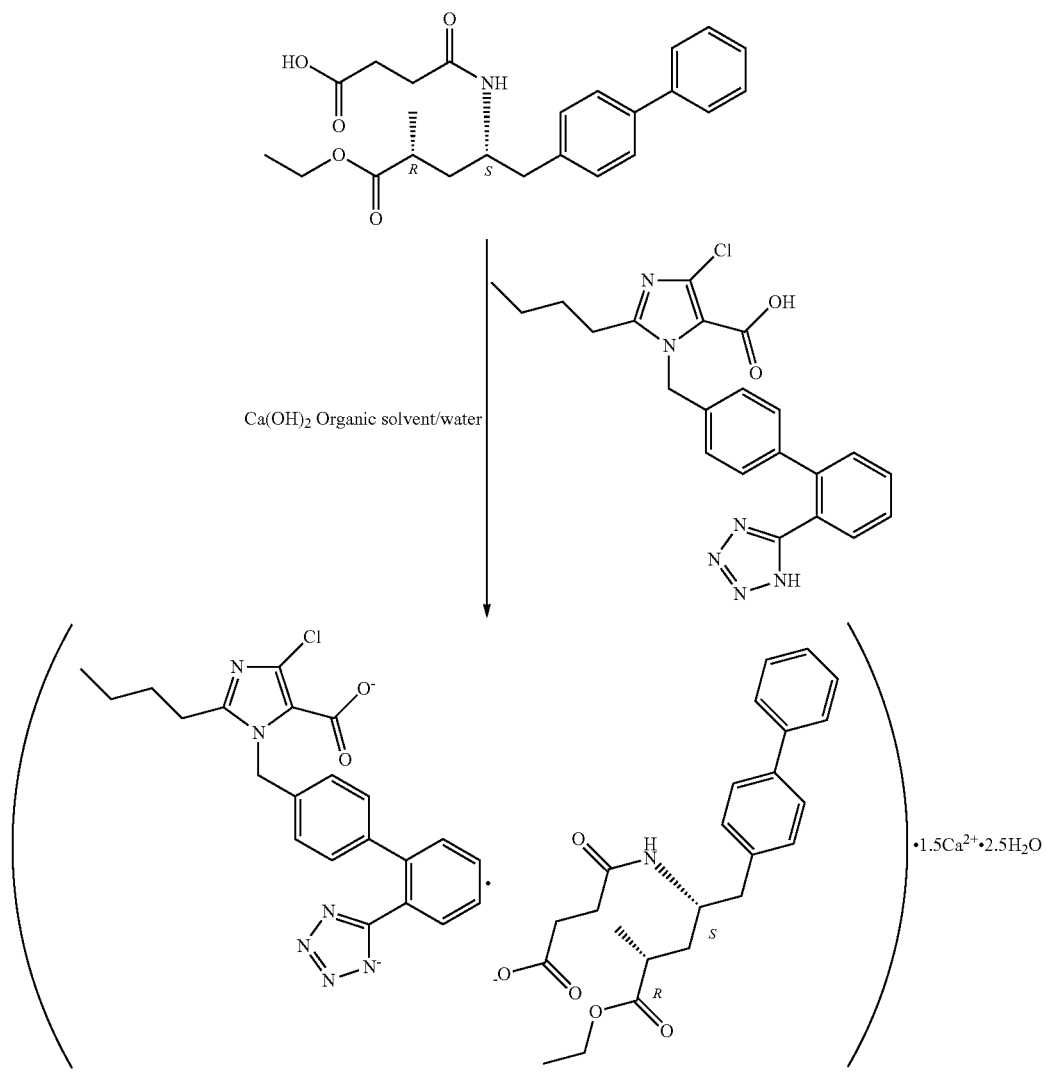

Specifically, XRD spectrum showed diffraction peaks with comparatively strong absorption intensity at 4.350, 5.150, 5.90°, 12.800 and 15.85° with the acceptable error range of +0.2°. Furthermore, the XRD spectrum of the supramolecular complex (compound) also showed diffraction peaks with comparatively strong repeatability at 9.00°, 10.150 and 15.02° with the acceptable error range of ±0.20; more specifically, the XRD spectrum shown in FIG. 1 showed the following peaks:

TABLE 1

Peak in XRD spectrum of product obtained in Example 2

| Number | 2θ (°, ±0.2) | Relative intensity (%) |
|---|---|---|
| 1 | 4.35 | 70.97 |
| 2 | 5.15 | 100.00 |
| 3 | 5.90 | 32.67 |
| 4 | 9.00 | 2.80 |
| 5 | 10.15 | 3.40 |
| 6 | 12.80 | 5.21 |
| 7 | 15.02 | 5.59 |
| 8 | 15.85 | 8.27 |
| 9 | 16.81 | 2.57 |
| 10 | 20.27 | 2.39 |
| 11 | 22.09 | 2.48 |
| 12 | 23.79 | 1.34 |
| 13 | 26.22 | 1.87 |

The Raman spectrum of product obtained showed diffraction peaks at the wavelength ($cm^{-1}$) of 3,061 (m), 2,935 (m, wide), 1,613 (st), 1,521 (m), 1,482 (w), 1,286 (m), 995 (w), 816 (w, wide), and 408 (w).

The infrared spectrum ($cm^{-1}$) of product obtained showed diffraction peaks at the important waveband of 3,383 (st, wide), 1,709 (m), 1,634 (m), 1,577 (st), 1,549 (st), 1,459 (st), 1,407 (st), 1,262 (m), 1,173 (w), 762 (m), 698 (w), etc. The intensities at the absorption waveband were expressed as below, (w)=weak, (m)=medium and (st)=strong.

Elemental analysis: measured values: C: 57.81%; H: 5.48%; N: 10.36%; theoretical value (calculated on $(EXP3174.AHU377)^{3-}.1.5Ca^{2+}.2.5H_2O$): C: 58.08%; H: 5.47%; N: 10.31%.

Figure 4:
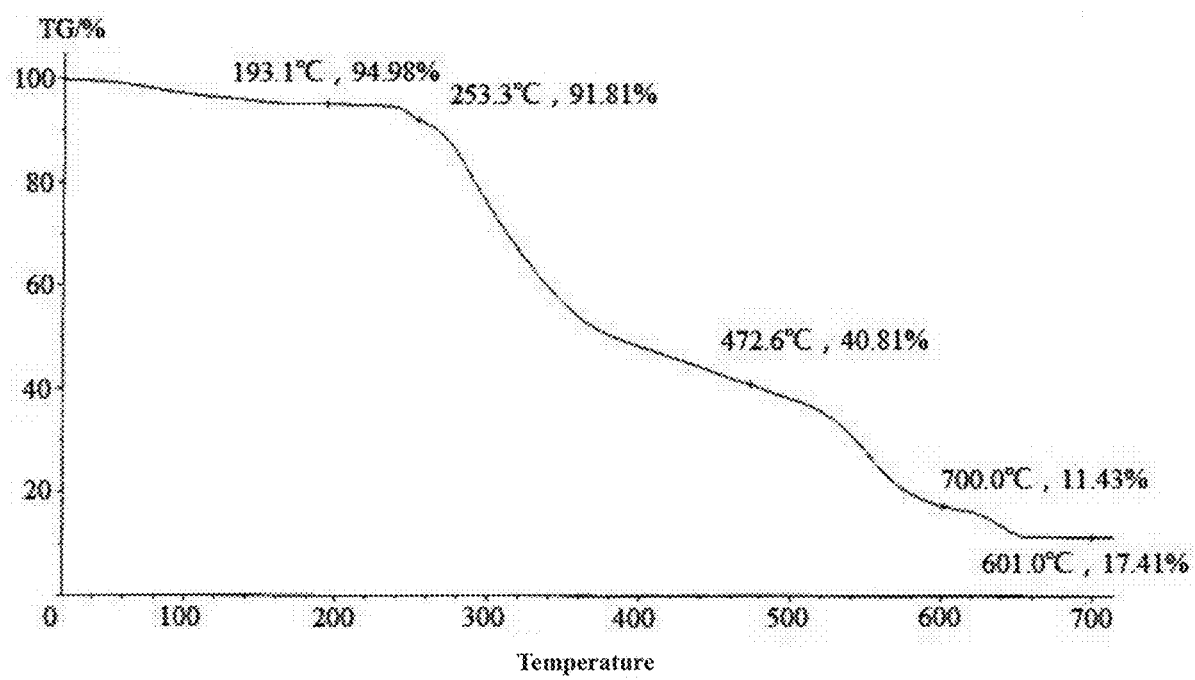
FIG. 4 TG spectrum of compound obtained in Example 2

TG spectrum of product obtained was shown in FIG. 4, and water content determined by TG was 5.0%.

Water content determined by Karl Fischer method was 4.9%.

Calcium content determined by atomic absorption method was 6.46%.

The formula unit of the compound described was $(EXP3174.AHU377)^{3-}.1.5Ca^{2+}.2.5H_2O$, which was determined by comprehensive analysis.

Example 3

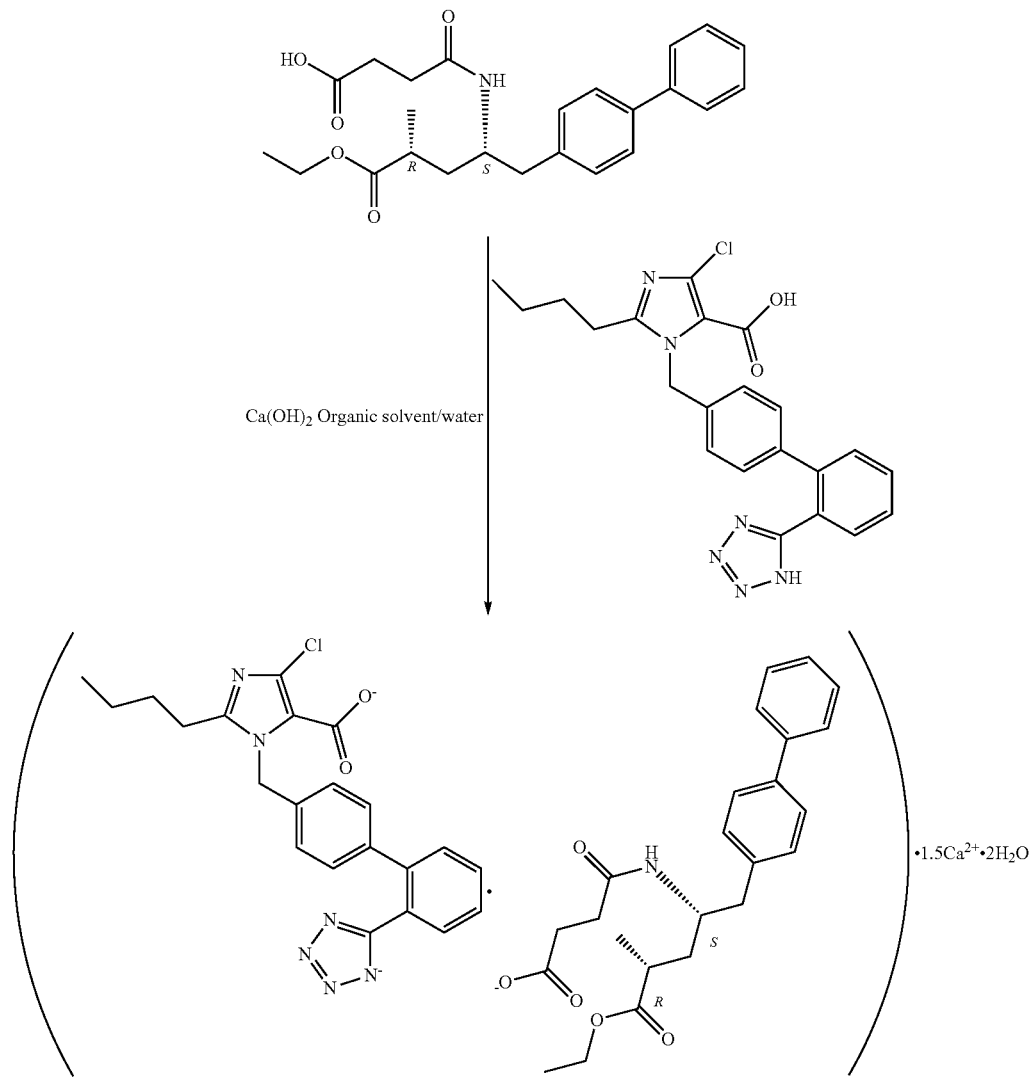

Under room temperature, 2.36 g of AHU377 free acid obtained in accordance with the method in Example 1, 2 g of EXP3174 and 40 mL of acetone were added to a 250 mL three-mouth flask, and mixture was dissolved to clarification; under room temperature, 1.6 equivalent calcium hydroxide solid corresponding to AHU377 and 0.6 mL of water were added, being stirred for 6 h at 35° C., 40 mL of acetone was supplemented, then being reacted for 8 h, through a Buchner funnel was filtered under the protection of nitrogen, the solid was washed with acetone to obtain white solid, 3.1 g solid was obtained after being dried under vacuum at 50° C. for 8 h, and the molar ratio of EXP3174 to AHU377 in the product obtained was 1:1 via calculation.

Figure 6:
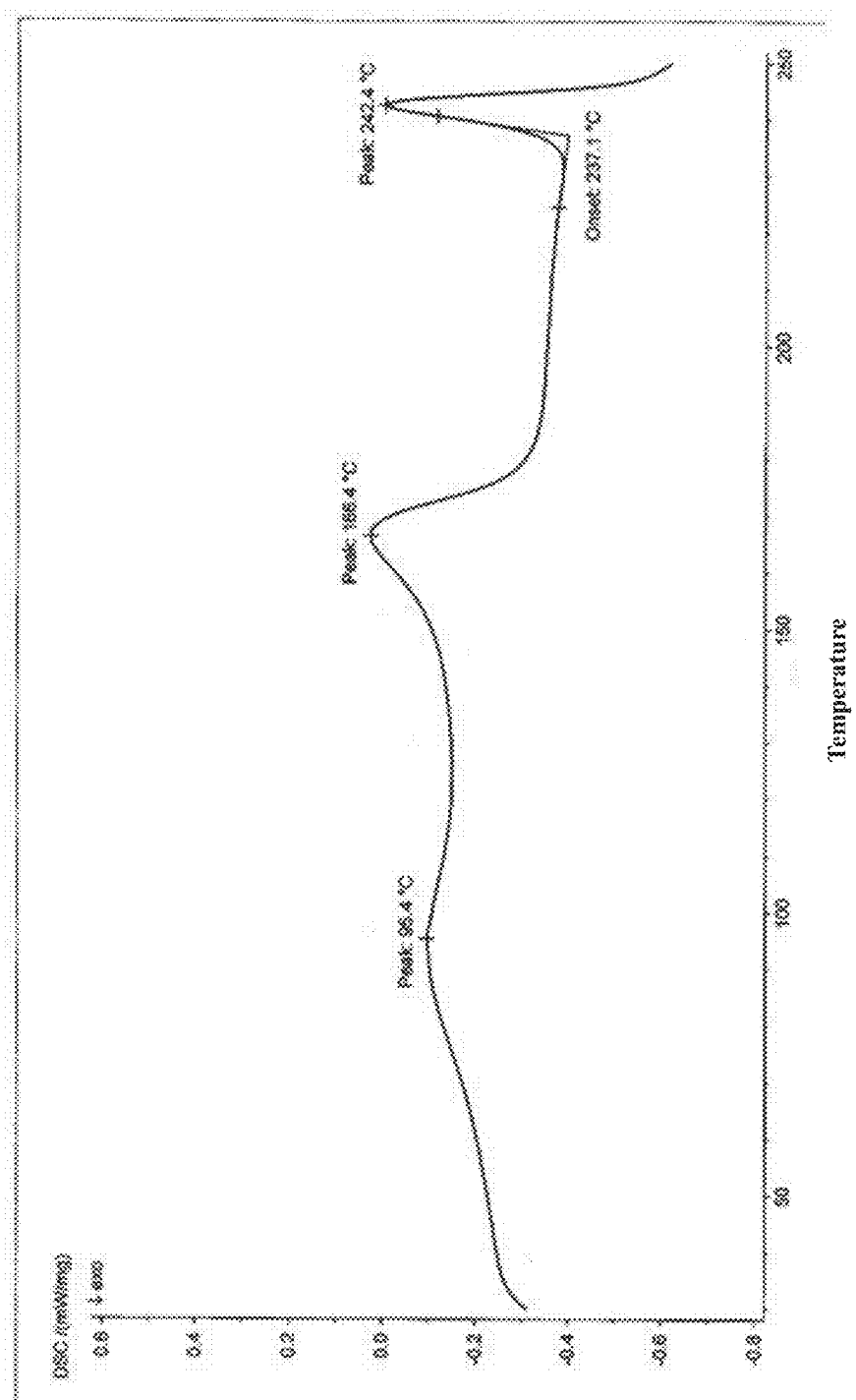
FIG. 6 DSC spectrum of compound obtained in Example 3

DSC spectrum of the product obtained was shown in FIG. 6.

Elemental analysis: measured values: C: 58.51%; H: 5.41%; N: 10.25%; theoretical values (calculated on $(EXP3174.AHU377)^{3-}.1.5Ca^{2+}.2H_2O$): C: 58.68%; H: 5.46%; N: 10.41%.

Figure 7:
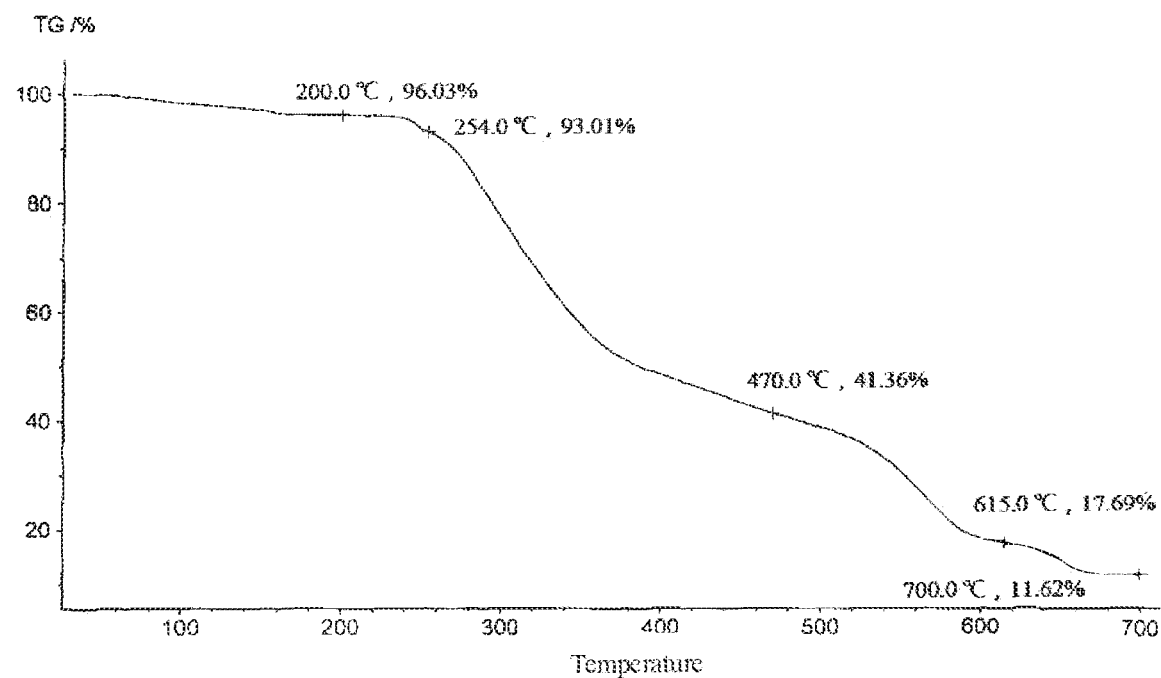
FIG. 7 TG spectrum of compound obtained in Example 3

TG spectrum of product obtained was shown in FIG. 7, and water content determined by TG was 3.97%.

Water content determined by Karl Fischer method was 3.83%.

Calcium content determined by atomic absorption method was 6.50%.

The formula unit of the compound described was $(EXP3174.AHU377)^{3-}.1.5Ca^{2+}.2H_2O$, which was determined by comprehensive analysis.

Figure 5:
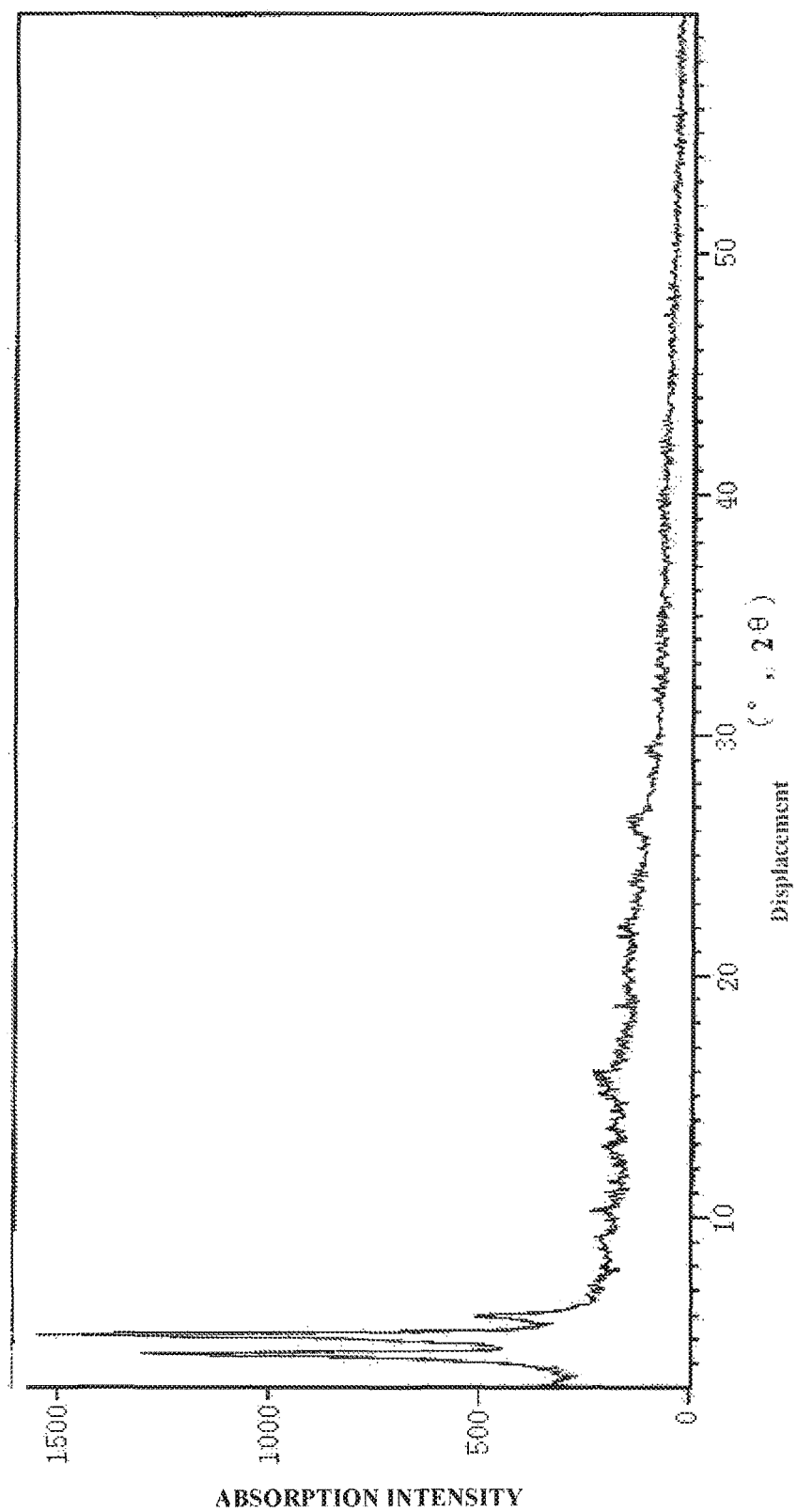
FIG. 5 XRD spectrum of compound obtained in Example 3

XRD spectrum of the product obtained tended to be consistent with that of the product obtained in Example 2 (as shown in FIG. 5), specifically, the XRD spectrum of the supramolecular compound (complex) showed diffraction peaks with comparatively strong absorption intensity at 4.40°, 5.19° and 5.96° with the acceptable error range of ±0.2°. Furthermore, the XRD spectrum of the supramolecular compound (complex) also showed diffraction peaks with comparatively strong repeatability at 15.82° and 26.34° with the acceptable error range of ±0.2°; more specifically, the XRD spectrum shown in FIG. 5 showed the following peaks:

| Number | 2θ (°, ±0.2) | Relative intensity (%) |
|---|---|---|
| 1 | 4.40 | 77.30 |
| 2 | 5.19 | 100.00 |
| 3 | 5.96 | 19.78 |
| 4 | 15.82 | 5.11 |
| 5 | 26.34 | 3.44 |

Example 4

Preparation of Compound:

Under room temperature, 2.40 g of AHU377 free acid obtained in accordance with the method in Example 1, 2 g of EXP3174, 40 mL of acetone and 10 mL of isopropanol were added to a 250 mL three-mouth flask, and the mixture was dissolved to clarification; under room temperature, 1.5 equivalent calcium hydroxide solid corresponding to AHU377 and 1 mL of water were added, being stirred for 6 h at 40° C., 40 mL of acetone was supplemented, then being reacted for 8 h, through a Buchner funnel was filtered under protection of nitrogen, the solid was washed with acetone to obtain white solid, 3.3 g solid was obtained after being dried under vacuum at 35° C. for 16 h with the purity of 99% by test of HPLC, and the molar ratio of EXP3174 to AHU377 in the product obtained was 1:1 by calculation.

XRD spectrum, DSC spectrum, Raman spectrum and infrared spectrum of the product obtained tended to be consistent with those of the product obtained in Example 2.

The formula unit of compound described was $(EXP3174.AHU377)^{3-}.1.5Ca^{2+}.2.5H_2O$, which was determined by combining of elemental analysis, water content test, and calcium content.

Example 5

Under room temperature, 2.4 g of AHU377 free acid obtained in accordance with the method in Example 1, 2.1 g of EXP3174, and 50 mL of isopropanol were added to a 250 mL three-mouth flask, and the mixture was dissolved to clarification; under room temperature, 1.4 equivalent calcium hydroxide solid corresponding to AHU377 and 0.6 mL of water were added, being stirred overnight at room temperature, about 40 mL of isopropanol was supplemented, then being reacted for 8 h, through a Buchner funnel was filtered under protection of nitrogen, the solid was washed with acetone to obtain white solid, 2.8 g solid was obtained after being dried under vacuum at 50° C. for 10 h, and the molar ratio of EXP3174 to AHU377 in the product obtained was 1:1 via calculation.

XRD spectrum, and DSC spectrum of the product obtained tended to be consistent with that of the product obtained in Example 3.

The formula unit of compound described was $(EXP3174.AHU377)^{3-}.1.5Ca^{2+}.2H_2O$, which was determined by combining of elemental analysis, water content test and calcium content test.

Comparative Example 1

EXP3174-AHU377 sodium salt compounds was tried to be prepared in accordance to the rate of added amount and preparation steps in each example of patent WO2007056546, and the results were as below:

TABLE 2

| Rate of charge and reaction results | | | |
|---|---|---|---|
| Number | Rate of charge Preparation steps | Solvent system | Results |
| 1 | WO2007056546 Example 1 | | No solid precipitated |
| 2 | WO2007056546 Example 2 | | Non-compound solid precipitation |
| 3 | WO2007056546 Example 3 | | No solid precipitated |

TABLE 2-continued

Rate of charge and reaction results

| Number | Rate of charge | Preparation steps | Solvent system | Results |
|---|---|---|---|---|
| 4 | WO2007056546 Example 1 | WO2007056546 Example 1 | Isopropyl ether | Non-compound solid precipitation |
| 5 | WO2007056546 Example 1 | WO2007056546 Example 1 | Acetonitrile | Non-compound solid precipitation |
| 6 | WO2007056546 Example 1 | WO2007056546 Example 1 | Ethyl acetate | Non-compound solid precipitation |
| 7 | WO2007056546 Example 1 | WO2007056546 Example 1 | Dichloromethane | Non-compound solid precipitation |
| 8 | WO2007056546 Example 1 | WO2007056546 Example 1 | Isopropyl acetate | Non-compound solid precipitation |
| 9 | WO2007056546 Example 1 | WO2007056546 Example 1 | Tetrahydrofuran | No solid precipitated |
| 10 | WO2007056546 Example 1 | WO2007056546 Example 1 | N-butyl alcohol | No solid precipitated |

The inventor failed to obtain sodium ion participated supramolecular complex (compound) after trying many methods; also, the inventor also failed to obtain potassium ion participated supramolecular complex (compound) after trying many methods.

Example 6

The anti-heart failure activity (short term, acute) of compounds obtained in Examples 2 and 3 was further tested in animal model (rat).

The animal model with heart failure using ligation of left anterior descending coronary artery was prepared, the therapeutic drug to the modeling animal was administrated by pre-gavage, once per day for 7 continuous days, and was continuously administrated for three days after successful modeling.

Details were as follows:

1. Laboratory Animal

SD male rats aged 6-week old;

2. Experimental Method

Pre-test preparation: All animals were divided into 5 groups by randomized blocks, 6 rats in each group, and the animals were acclimated for 3 days before test treatment; Experimental process: Therapeutic drug was given to the test animals by pre-gavage, once per day for 7 continuous days. Operation was conducted on Day 8, the animals were anesthetized, trachea was connected to a respirator, electrocardiograph (ECG) was connected for real-time recording, thoracic cavity was opened between the 3rd and 4th ribs, left anterior descending coronary artery was ligated, ST segment elevation of ECG indicated successful ligation, the thoracic cavity was closed, and the skin was sutured;

Therapeutic drug was continuously given to the animals by gavage after operation once per day for 3 continuous days. The animals were anesthetized on Day 11, ECG was measured, and then arterial pressure and left ventricular pressure were measured by carotid artery intubation.

3. Data Record

Blood pressure: mean arterial pressure (mAP) and mean left ventricular pressure, the data in each group were as below:

TABLE 3

Data on anti-heart failure activity (short term, acute) in animal model (rat)

| Group | Administration dose (mg/kg) | mAP (mmHg) | mLVP (mmHg) |
|---|---|---|---|
| Untreated thoracotomy group | — | 111 | 69 |
| EXP3174 | 30 | 106 | 61 |
| AHU377 calcium salt | 30 | 104 | 63 |
| LCZ696 | 68 | 78 | 44 |
| Example 2 compound group 1 | 22 | 85 | 53 |
| Example 2 compound group 2 | 67 | 78 | 43 |
| Example 3 compound group 1 | 22 | 87 | 52 |
| Example 3 compound group 2 | 67 | 75 | 45 |

From the results above, we observed that the post-modeling animals with ligation of coronary artery had compensatory elevation of blood pressure due to the damage of partial myocardial function. The person skilled in the art could understand that, in the test protocol of anti-heart failure activity (short-term, acute) in animal model (rat), short-term administration significantly affected the blood pressure of test animals, the therapeutic effect on heart failure was firstly embodied as the effect on lowering blood pressure, therefore, the experimental result was in accordance with what is expected; From the data obtained, we observed that the improvement effect of single medication of EXP3174 and AHU377 calcium salt on mAP and mLVP were not significant compared with those in untreated animal group, while the effect on lowering blood pressure in Examples 2 and 3 compound groups were significant, and showed dose-dependent by comparison of different doses; subsequent further test found that the weight of test animals in corresponding group were also significantly increased compared with those in untreated group.

Example 7

The anti-heart failure activity (long term, chronic) of compounds obtained in Example 2 and Example 3 were further tested in animal model (rat).

The animal model with heart failure using ligation of left anterior descending coronary artery was prepared, the therapeutic drug was administered to the animals by gavage after one week of postoperative recovery, once per day for 4 continuous weeks, the effect of primary heart failure indexes of test animals, such as heart rate, area of myocardial fibrosis, ejection fraction, thickness of heart wall were recorded, and the data obtained were as below:

TABLE 4

Data on anti-heart failure activity (long term, chronic) in animal model (rat)

| Group | Administration dose (mg/kg) | Heart rate (beats/min) | Myocardial fibrosis (%) | Ejection fraction (%) | Thickness of heart wall (cm) |
|---|---|---|---|---|---|
| Blank healthy group* | — | 419.7 | 3.24 | 87.2 | 0.214 |
| Model group** | — | 392.1 | 40.09 | 51.3 | 0.147 |
| Physical mixture group*** | 70 | 405.8 | 8.96 | 63.1 | 0.157 |
| EXP3174 | 30 | 427.8 | 62.89 | 47.9 | 0.136 |
| AHU377 calcium salt | 30 | 378.9 | 54.88 | 53.3 | 0.137 |
| LCZ696 | 68 | 412.9 | 11.51 | 70.6 | 0.169 |
| Example 2 compound group 1 | 22 | 414.9 | 7.56 | 66.6 | 0.178 |
| Example 2 compound group 2 | 67 | 423.2 | 4.22 | 65.9 | 0.164 |
| Example 3 compound group 1 | 22 | 417.3 | 7.37 | 65.3 | 0.181 |
| Example 3 compound group 2 | 67 | 422.5 | 4.17 | 66.8 | 0.169 |

*The rats were not administrated with drugs after thoracotomy.
**The rats were not administrated with drugs after thoracotomy and ligation.
***The physical mixture obtained from the mixing of EXP3174 and AHU377 calcium salts in the mass ratio of 1:1.

Above-mentioned experimental results showed that both the low dose (22 mg/kg) and the high dose (67 mg/kg) compound groups showed the efficacy of anti-chronic heart failure;

Specifically, being compared with the indexes of untreated rats in heart failure model group, those of animals in low dose (22 mg/kg) and high dose (67 mg/kg) compound groups were significantly improved, closing to those of animals in the sham-operation groups;

Being compared with indexes in single-drug group with the same dose, both the low-dose (22 mg/kg) and the high dose (67 mg/kg) groups could significantly and preferably delay the process of heart failure of rats, and showed significantly better anti-heart failure activity than single medication;

Most importantly, in the comparison with indexes of physical mixture, we were amazed to find that both the low dose (22 mg/kg) and the high dose (67 mg/kg) compound groups showed better therapeutic effects than other experimental groups, and more unexpectedly, low dose group showed better therapeutic effect than physical mixture; in the comparison with LCZ696 test group (68 mg/kg), we found the comprehensive performance in the same dose group (67 mg/kg) was slightly better, while, even the low dose group (22 mg/kg) also showed similar activity to the LCZ696 test group, and even showed slight advantage in some indexes, such as myocardial fibrosis, indicating that the supramolecular complexes (compounds) mentioned in this invention were potential to achieve the objective of reduction in clinical dosage.

Example 8

Hygroscopicity

Figure 8:
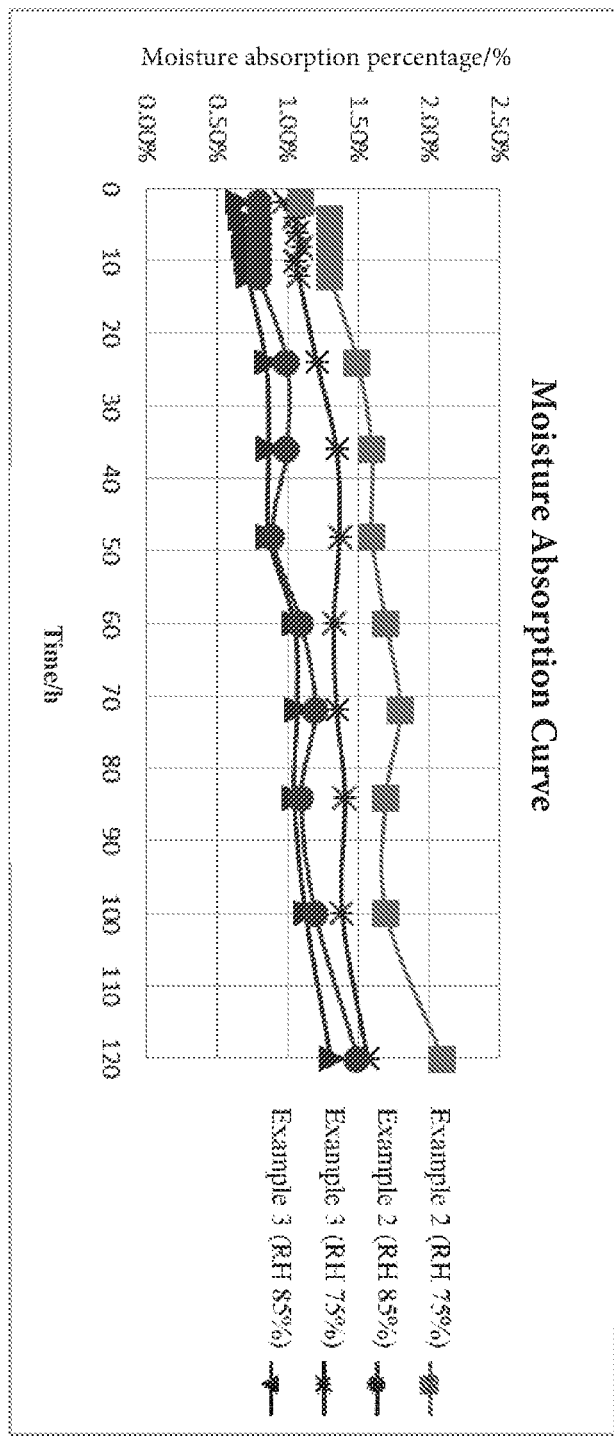
FIG. 8 Moisture absorption curves of compounds obtained in Example 2 and Example 3 under the environment of RH=75% and RH=85%

LCZ696 (purity: 99.4%) was prepared using the method disclosed in Example 1 of patent WO2007056546, respectively the hygroscopicity (plain sample) was tested together with the samples obtained in above-mentioned Example 2 and Example 3 under the conditions of RH 75% and RH 85%, and the results were shown in the table below (for moisture absorption curve, see FIG. 8):

TABLE 5

Comparison data of hygroscopicity

| Test sample | RH 75% (%) | | RH 85% (%) | |
|---|---|---|---|---|
| | Day 0 | Day 5 | Day 0 | Day 5 |
| LCZ696 | 4.9 | —* | 4.9 | — |
| Example 2 | 4.9 | +1.31%** | 4.9 | +1.57% |
| Example 3 | 3.83 | +1.50% | 3.83 | +2.10% |

*The sample converted to be solution (deliquescence), and the water content could not be tested.
**Water content increment.

From the table above, we observed that the supramolecular complexes (compounds) mentioned in this invention showed better-than-expected hygroscopicity (low) advantages under the conditions of RH 75% and RH 85%, specifically, even though the supramolecular complexes (compounds) obtained in Example 2 and Example 3 were exposed to the storage environment of RH 75% for 5 days, the mass increments were <2.00%, and when being exposed to the storage environment of RH 85%, the mass increments were <2.50%, being seen from the moisture absorption curves of both complexes, the mass increment of samples was gentle during the experiment, showing that the samples had improved hygroscopicity (lower); in addition, the purity of test samples also showed no significant changes in the content test simultaneously performed in the experiment;

However, for LCZ696, the test samples were failed to keep solid state till the end of the experiment, specifically, the test samples were completely deliquescent at the end of the experiment (in a soluble form), showing that its hygroscopicity (low) was far less than that of the supramolecular complexes (compounds) mentioned in this invention.

Flowability

LCZ696 was prepared using the method disclosed in Example 1 of patent WO2007056546, the samples obtained in above-mentioned Example 2 and Example 3 were crushed to the particle size distribution range similar to that of LCZ696, and the results were shown in the table below:

TABLE 6

Comparison data of flowability

| Test sample | Angle of repose (°) | Bulk density (g/ml) |
|---|---|---|
| LCZ696 | 57.35 | 0.527 |
| Example 2 | 44.79 | 0.641 |
| Example 3 | 43.64 | 0.630 |

From the data above, we observed that the supramolecular complexes (compounds) mentioned in this invention showed moderate flowability, and no obvious electrostatic phenomenon, and powder property was better than that of LCZ696; however, for LCZ696, it showed stagnant during the test of angle of repose thus to cause difficulties while laying-off, its angle of repose determined was 57.35° after hard laying-off, the powder showed electrostatic phenomenon with less bulk density, and the powder properties were poorer than that of supramolecular complexes (compounds) obtained in Example 2 and Example 3.

Example 9

Accelerated Stability Test the supramolecular complexes (compounds) obtained in Example 2 and Example 3 were stored under the conditions of 40° C., 75% RH for 6 months to test the storage stability under accelerated conditions (with package), and the results were shown in the table below:

TABLE 7

Accelerated stability data

| Sample | Day 0 | Day 30 | Day 180 |
|---|---|---|---|
| Example 2 | 99.85% | 99.79% | 99.84% |
| Example 3 | 99.91% | 99.94% | 99.90% |

Known from the data above, the supramolecular complexes (compounds) in this invention showed higher stability which met the requirements of clinical pharmaceutical preparation.

In conclusion, it showed that the series of supramolecular complexes (compounds) in this invention had better anti-acute heart failure and chronic heart failure effects with fewer administration dose, which are helpful to reduce the drug dosage; they showed greater advantages in hygroscopic property (lower) than those of the predicate products opened in existing technologies, also showed advantages in powder properties (flowability, bulk density, etc.), and showed physicochemical properties more convenient for production; we could know that the series of supramolecular complexes (compounds) in this invention had better prospect in clinical medication.

The mentioned examples above were the relatively good implementation ways in this invention, while the implementation ways in this invention were not restricted by above-mentioned Examples, any other change, modification, replacement, combination and simplification without departing from the spirit and principle in this invention were also included in the protection range of the invention.

The invention claimed is:

1. A supramolecular complex of angiotensin II receptor metabolite and NEP inhibitor, wherein the formula unit of the supramolecular complex is:

(aEXP3174.bAHU377).xCa.nA, wherein the molar ratio of a to b is from 1:0.25 to 1:4, x is from 0.5 to 3, A is water, methanol, ethanol, 2-propyl alcohol, acetone, ethyl acetate, methyl-tert-butyl ether, acetonitrile, methylbenzene or dichloromethane, and n is from 0 to 3.

2. The supramolecular complex of angiotensin II receptor metabolite and NEP inhibitor according to claim 1, wherein the formula unit of the supramolecular complex is:

(EXP3174.AHU377).xCa.nH$_2$O, wherein x is from 0.5 to 2, and n is from 0 to 3.

3. The supramolecular complex of angiotensin II receptor metabolite and NEP inhibitor according to claim 2, wherein x is from 1.5 to 2 and n is from 1 to 3.

4. The supramolecular complex of angiotensin II receptor metabolite and NEP inhibitor according to claim 2, wherein n is from 2 to 3.

5. The supramolecular complex of angiotensin II receptor metabolite and NEP inhibitor according to claim 1, wherein the formula unit of the supramolecular complex is:

(EXP3174.AHU377).1.5Ca.nH$_2$O, wherein n is from 1 to 3.

6. The supramolecular complex of angiotensin II receptor metabolite and NEP inhibitor according to claim 5, wherein n is from 2 to 3.

7. The supramolecular complex of angiotensin II receptor metabolite and NEP inhibitor according to claim 1, wherein the formula unit of the supramolecular complex is:

(EXP3174.AHU377).2Ca.nH$_2$O, wherein n is from 1 to 3.

8. The supramolecular complex of angiotensin II receptor metabolite and NEP inhibitor according to claim 7, wherein n is from 2 to 3.

9. The supramolecular complex of angiotensin II receptor metabolite and NEP inhibitor according to claim 1, wherein the formula unit of the supramolecular complex is any one of:

(EXP3174.AHU377).1.5Ca.1H$_2$O (EXP3174.AHU377).1.5Ca.1.5H$_2$O (EXP3174.AHU377).1.5Ca.2H$_2$O (EXP3174.AHU377).1.5Ca.2.5H$_2$O (EXP3174.AHU377).1.5Ca.3H$_2$O (EXP3174.AHU377).2Ca.1H$_2$O (EXP3174.AHU377).2Ca.1.5H$_2$O (EXP3174.AHU377).2Ca.2H$_2$O (EXP3174.AHU377).2Ca.2.5H$_2$O, and (EXP3174.AHU377).2Ca.3H$_2$O.

10. The supramolecular complex of angiotensin II receptor metabolite and NEP inhibitor according to claim 1, wherein an XRD spectrum of the supramolecular complex shows diffraction peaks at 4.35°, 5.15°, 5.90°, 12.80° and 15.85° with an acceptable error range of ±0.2°, or wherein an XRD spectrum of the supramolecular complex shows diffraction peaks at 4.40°, 5.19° and 5.96° with an acceptable error range of ±0.2°.

11. The supramolecular complex of angiotensin II receptor metabolite and NEP inhibitor according to claim 10, wherein the XRD spectrum of the supramolecular complex that shows diffraction peaks at 4.35°, 5.15°, 5.90°, 12.80° and 15.85° with an acceptable error range of ±0.2° also shows diffraction peaks at 9.00°, 10.15° and 15.02° with an acceptable error range of ±0.2°, or wherein the XRD spectrum of the supramolecular complex that shows diffraction peaks at 4.40°, 5.19° and 5.96° with an acceptable error range of ±0.2° also shows diffraction peaks at 15.82° and 26.34° with an acceptable error range of ±0.2°.

12. The supramolecular complex of angiotensin II receptor metabolite and NEP inhibitor according to claim 10, wherein the XRD spectrum of the supramolecular complex shows diffraction peaks of:

| Number | 2θ (°, ±0.2) | Relative intensity (%) |
|---|---|---|
| 1 | 4.35 | 70.97 |
| 2 | 5.15 | 100.00 |
| 3 | 5.90 | 32.67 |
| 4 | 9.00 | 2.80 |
| 5 | 10.15 | 3.40 |
| 6 | 12.80 | 5.21 |
| 7 | 15.02 | 5.59 |
| 8 | 15.85 | 8.27 |
| 9 | 16.81 | 2.57 |
| 10 | 20.27 | 2.39 |
| 11 | 22.09 | 2.48 |
| 12 | 23.79 | 1.34 |
| 13 | 26.22 | 1.87 | or wherein the XRD spectrum of the supramolecular complex shows diffraction peaks of:

| Number | 2θ (°, ±0.2) | Relative intensity (%) |
|---|---|---|
| 1 | 4.40 | 77.30 |
| 2 | 5.19 | 100.00 |
| 3 | 5.96 | 19.78 |
| 4 | 15.82 | 5.11 |
| 5 | 26.34 | 3.44 |

13. The supramolecular complex of angiotensin II receptor metabolite and NEP inhibitor according to claim 10, wherein the XRD spectrum of the supramolecular complex is as shown in FIG. 1 or FIG. 5.

14. The supramolecular complex of angiotensin II receptor metabolite and NEP inhibitor according to claim 1, wherein a DSC spectrum of the supramolecular complex shows two dehydration endothermic peaks at 94.4±10° C. and 164.1±10° C., and an endothermic peak in the spectrum at 244.6±5° C.; or wherein a DSC spectrum of the supramolecular complex shows two dehydration endothermic peaks at 95.4±10° C. and 166.4±10° C., and an endothermic peak in the spectrum at 242.4±5° C.

15. The supramolecular complex of angiotensin II receptor metabolite and NEP inhibitor according to claim 14, wherein the DSC spectrum of the supramolecular complex is as shown in FIG. 2 or FIG. 6.

16. A composition comprising a supramolecular complex of an angiotensin II receptor metabolite and a NEP inhibitor according to claim 1 and a pharmaceutically acceptable carrier.

17. A method of treating heart failure or hypertension in a patient comprising administering to said patient a drug preparation comprising the supramolecular complex of angiotensin II receptor metabolite and NEP inhibitor according to claim 1 and a carrier.

18. The method according to claim 17, wherein the mass percentage of the supramolecular complex in the drug is 0.1-99.9%.

19. A method of preparing a supramolecular complex of angiotensin II receptor metabolite and NEP inhibitor according to claim 1, comprising:
   1) freeing a salt of AHU377 to provide AHU377;
   2) dissolving the AHU377 1) and EXP3174 in a first solvent;
   3) dissolving or suspending a pharmaceutically acceptable calcium ionic salt in a second solvent;
   4) adding the solution or suspension of 3) to the solution of 2) and, optionally, adding a calcium ionic salt in a solid form to the mixture;
   5) stirring the mixture, filtering the mixture to obtain a solid, and drying the solid to provide a supramolecular complex of angiotensin II receptor metabolite and NEP inhibitor according to claim 1,
   wherein
      the salt of AHU377 is selected from a calcium salt, a magnesium salt, a zinc salt, a ferric salt, a sodium salt, an ammonium salt, a diethylammonium salt, or a triethylammonium salt,
      the first solvent is isopropyl acetate,
      the molar ratio of EXP3174 to AHU377 in 2) is 0.7-1.2:1,
      the molar ratio of quantity of calcium ion in calcium ionic salt to AHU377 is 1.3-2.1:1,
      the second solvent comprises acetone and/or isopropanol and a suitable quantity of water, wherein a weight/volume ratio of AHU377 to water is 1-8:1 g/ml,
      the formula unit of the supramolecular complex obtained from the reaction is (EXP3174.AHU377).1.5Ca.2.5H$_2$O, and
      the reaction temperature in step 4) is between room temperature and 45° C.

20. The method according to claim 19, wherein the weight/volume ratio of AHU377 to water is 2.36:1 g/ml.

21. A method of preparing a supramolecular complex of angiotensin II receptor metabolite and NEP inhibitor according to claim 1, comprising:
   1) freeing a salt of AHU377 to provide AHU377;
   2) dissolving the AHU377 of 1) and EXP3174 in a solvent;
   3) adding a calcium ionic salt in a solid form in a solid form to the solution of 2);
   4) stirring the mixture, filtering the mixture to obtain a solid, and drying the solid to provide a supramolecular complex of angiotensin II receptor metabolite and NEP inhibitor according to claim 1,
   wherein
      the salt of AHU377 is selected from a calcium salt, a magnesium salt, a zinc salt, a ferric salt, a sodium salt, an ammonium salt, a diethylammonium salt, or a triethylammonium salt, the solvent comprises isopropyl acetate and sufficient water, wherein a weight/volume ratio of AHU377 to water is 1-8:1 g/ml, the molar ratio of EXP3174 to AHU377 is 0.7-1.2:1;

the molar ratio of quantity of calcium ion in calcium ionic salt to AHU377 is 1.3-2.1:1, the formula unit of the supramolecular complex obtained from the reaction is (EXP3174.AHU377).1.5Ca.2H$_2$O, and the reaction temperature in 3) is between room temperature and 45° C.

22. The method according to claim 21, wherein the weight/volume ratio of AHU377 to water is 3.93:1 g/ml.

* * * * *